United States Patent
Stahmann et al.

(10) Patent No.: US 8,027,719 B2
(45) Date of Patent: Sep. 27, 2011

(54) METHOD AND APPARATUS FOR DELIVERING DEFIBRILLATION SHOCK THERAPY WHILE REDUCING ELECTRICAL DISPERSION DUE TO VENTRICULAR CONDUCTION DISORDER

(75) Inventors: Jeffrey E. Stahmann, Ramsey, MN (US); Jesse W. Hartley, Lino Lakes, MN (US); Steven D. Girouard, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 540 days.

(21) Appl. No.: 12/051,997

(22) Filed: Mar. 20, 2008

(65) Prior Publication Data

US 2008/0167692 A1 Jul. 10, 2008

Related U.S. Application Data

(63) Continuation of application No. 10/746,856, filed on Dec. 24, 2003, now Pat. No. 7,349,734, which is a continuation-in-part of application No. 09/748,796, filed on Dec. 26, 2000, now Pat. No. 7,142,918, and a continuation-in-part of application No. 09/571,676, filed on May 15, 2000, now Pat. No. 6,721,596.

(51) Int. Cl.
*A61N 1/00* (2006.01)
(52) U.S. Cl. ........................................... 607/5
(58) Field of Classification Search .............. 607/5, 14, 607/25
See application file for complete search history.

(56) References Cited

U.S. PATENT DOCUMENTS

| | | | |
|---|---|---|---|
| 4,059,116 A | 11/1977 | Adams | |
| 4,485,818 A | 12/1984 | Leckrone et al. | |
| 4,830,006 A | 5/1989 | Haluska et al. | |
| 4,860,749 A | 8/1989 | Lehmann | |
| 4,928,688 A | 5/1990 | Mower | |
| 4,932,406 A | 6/1990 | Berkovits | |
| 4,944,298 A | 7/1990 | Sholder | |
| 4,998,974 A | 3/1991 | Aker | |
| 5,133,350 A | 7/1992 | Duffin | |
| 5,144,949 A | 9/1992 | Olson | |
| 5,226,415 A | 7/1993 | Girodo et al. | |
| 5,282,836 A | 2/1994 | Kreyenhagen et al. | |

(Continued)

FOREIGN PATENT DOCUMENTS

EP 0401962 A2 12/1990

(Continued)

OTHER PUBLICATIONS

Alonso, C., "Electrocardiographic Predictive Factors of Long-Term Clinical Improvement with Multisite Biventricular Pacing in Advanced Heart Failure", *The American Journal of Cardiology* (US), vol. 84, No. 12, (Dec. 1999), 1417-1421.

(Continued)

*Primary Examiner* — George Manuel
(74) *Attorney, Agent, or Firm* — Schwegman, Lundberg & Woessner, P.A.

(57) ABSTRACT

A method and device for delivering defibrillation shock therapy in patients having an inter-ventricular conduction disorder is presented. Ventricular resynchronization therapy is employed to reduce the dispersion of ventricular depolarization which takes place due to the conduction disorder and reduces the safety margin of shocks delivered synchronously with ventricular beats. The method may be employed in the treatment of atrial or ventricular tachyarrhythmias.

20 Claims, 3 Drawing Sheets

U.S. PATENT DOCUMENTS

| | | | |
|---|---|---|---|
| 5,411,531 A | 5/1995 | Hill et al. |
| 5,507,784 A | 4/1996 | Hill et al. |
| 5,549,649 A | 8/1996 | Florio et al. |
| 5,584,867 A | 12/1996 | Limousin et al. |
| 5,690,686 A | 11/1997 | Min et al. |
| 5,713,930 A | 2/1998 | van der Veen et al. |
| 5,713,932 A | 2/1998 | Gillberg et al. |
| 5,716,383 A | 2/1998 | Kieval et al. |
| 5,730,142 A | 3/1998 | Sun et al. |
| 5,749,906 A | 5/1998 | Kieval et al. |
| 5,755,736 A | 5/1998 | Gillberg et al. |
| 5,782,888 A | 7/1998 | Sun et al. |
| 5,792,193 A | 8/1998 | Stoop |
| 5,814,077 A | 9/1998 | Sholder et al. |
| 5,814,085 A | 9/1998 | Hill |
| 5,871,507 A | 2/1999 | Obel et al. |
| 5,876,422 A | 3/1999 | Van Groeningen |
| 5,893,882 A | 4/1999 | Peterson et al. |
| 5,931,856 A | 8/1999 | Bouhour et al. |
| 5,968,081 A | 10/1999 | Levine |
| 5,999,850 A | 12/1999 | Dawson et al. |
| 6,081,748 A | 6/2000 | Struble et al. |
| 6,122,545 A | 9/2000 | Struble et al. |
| 6,219,579 B1 | 4/2001 | Bakels et al. |
| 6,223,079 B1 | 4/2001 | Bakels et al. |
| 6,223,082 B1 | 4/2001 | Bakels et al. |
| 6,238,420 B1 | 5/2001 | Bakels et al. |
| 6,285,907 B1 | 9/2001 | Kramer et al. |
| 6,370,431 B1 * | 4/2002 | Stoop et al. | 607/14 |
| 6,411,847 B1 | 6/2002 | Mower |
| 6,424,865 B1 | 7/2002 | Ding |
| 6,430,438 B1 | 8/2002 | Chen et al. |
| 6,434,424 B1 | 8/2002 | Igel et al. |
| RE38,119 E | 5/2003 | Mower |
| 6,671,549 B2 * | 12/2003 | Van Dam et al. | 607/25 |
| 6,721,596 B1 | 4/2004 | Girouard et al. |
| 6,847,842 B1 | 1/2005 | Rodenhiser et al. |
| 7,062,325 B1 | 6/2006 | Krig et al. |
| 7,142,918 B2 | 11/2006 | Stahmann et al. |
| 7,181,278 B2 | 2/2007 | Kramer et al. |
| 7,349,734 B2 * | 3/2008 | Stahmann et al. | 607/5 |
| 7,805,192 B2 | 9/2010 | Stahmann et al. |
| 2004/0215245 A1 | 10/2004 | Stahmann et al. |

FOREIGN PATENT DOCUMENTS

| | | |
|---|---|---|
| WO | WO-00/04950 A2 | 2/2000 |
| WO | WO-00/38782 A1 | 7/2000 |
| WO | WO-00/71203 A1 | 11/2000 |

OTHER PUBLICATIONS

Das, G., "QT Interval and Repolarization Time in Patients With Intraventricular Conduction Delay", *J Electrocardiol.*, 23(1), (1990), 49-52.

U.S. Appl. No. 10/214,474, filed Aug. 8, 2002, entitled "*Method and Apparatus for Treating Hemodynamic Disfunction* ", 3 pgs.

Prinzen, F. W., et al., "Optimization of Ventricular Function by Improving the Activation Sequence During Ventricular Pacing", *Pacing Clin Electrophysiol.*, 21(11 Pt 2), (1998), 2256-2260.

Saxon, L. A., et al., "Acute Effects of Intraoperative Multisite Ventricular Pacing on Left Ventricular Function and Activation/Contraction Sequence in Patients with Depressed Ventricular Function.", *J Cardiovasc Electrophysiol.*, 9(1), (1998), 13-21.

Stahmann, Jeffrey, et al., "Apparatus and Method for Pacing Mode Switching During Atrial Tachyarrhythmias", U.S. Appl. No. 11/549,368, filed Oct. 13, 2006, 25 pgs.

"U.S. Appl. No. 11/549,368, Notice of Allowance mailed Feb. 1, 2010", 7 pgs.

"U.S. Appl. No. 11/549,368, Notice of Allowance mailed May 17, 2010", 4 pgs.

"U.S. Appl. No. 12/891,669, Non Final Office Action mailed Dec. 15, 2010", 6 pgs.

* cited by examiner

METHOD AND APPARATUS FOR DELIVERING DEFIBRILLATION SHOCK THERAPY WHILE REDUCING ELECTRICAL DISPERSION DUE TO VENTRICULAR CONDUCTION DISORDER

CROSS REFERENCE TO RELATED APPLICATIONS AND CLAIM FOR PRIORITY UNDER 35 U.S.C. 120

This application is a continuation of application Ser. No. 10/746,856, filed Dec. 24, 2003, now issued as U.S. Pat. No. 7,349,734, which application is a continuation-in-part of the following, commonly assigned patent applications: "Apparatus and Method for Pacing Mode Switching during Atrial Tachyarrhythmias," application Ser. No. 09/748,796, filed on Dec. 26, 2000, issued as U.S. Pat. No. 7,142,918, and "Atrial Shock Therapy with Ventricular Pacing," application Ser. No. 09/571,676, filed on May 15, 2000, issued as U.S. Pat. No. 6,721,596, the disclosures of which are hereby incorporated by reference.

FIELD OF THE INVENTION

This invention pertains to methods and apparatus for treating cardiac disease with electrical therapy.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include ventricular tachycardia, ventricular fibrillation (VF), atrial tachycardia, and atrial fibrillation (AF). Tachycardia is characterized by a rapid rate, either due to an ectopic excitatory focus or abnormal excitation by normal pacemaker tissue. Fibrillation occurs when the chamber depolarizes in a chaotic fashion with abnormal depolarization waveforms as reflected by an ECG.

An electrical shock applied to a heart chamber (i.e., a defibrillation or cardioversion, the terms used synonymously herein) can be used to terminate most tachyarrhythmias by simultaneously depolarizing all of the myocardium. Implantable cardioverter/defibrillators (ICDS) provide this kind of therapy by delivering a shock pulse to the heart when fibrillation is detected by the device. An ICD is a computerized device containing a pulse generator that is usually implanted into the chest or abdominal wall. Electrodes connected by leads to the ICD are placed on the heart, or passed transvenously into the heart, to sense cardiac activity and to conduct the shock pulses from the pulse generator. ICDs can be designed to treat either atrial or ventricular tachyarrhythmias, or both, and may also incorporate cardiac pacing functionality for treating bradycardia or providing cardiac resynchronization therapy.

The most dangerous tachyarrythmias are ventricular tachycardia and ventricular fibrillation, and ICDs have most commonly been applied in the treatment of those conditions. ICDs are also capable, however, of detecting atrial tachyarrhythmias, such as atrial fibrillation and atrial flutter, and delivering a shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy.

As aforesaid, an ICD terminates atrial fibrillation by delivering a shock pulse to electrodes usually disposed in or near the atria. The resulting depolarization also spreads to the ventricles, however, and there is a risk that such an atrial shock pulse can actually induce ventricular fibrillation, a condition much worse than atrial fibrillation. To lessen this risk, most current ICDs delay delivering an atrial shock pulse until the intrinsic ventricular rhythm is below a specified maximum rate and then deliver the shock synchronously with a sensed ventricular depolarization (i.e., an R wave). That is, an R-R interval, which is the time between a presently sensed R wave and the preceding R wave, is measured. If the R-R interval is above a specified minimum value, the interval is considered shockable and the atrial defibrillation shock pulse is delivered.

As explained below, certain patients suffer from inter-ventricular and/or intra-ventricular conduction deficits, characterized by a wide QRS complex on a surface electrocardiogram, which shortens the interval after an R wave in which an atrial defibrillation shock may be safely delivered. This either makes the delivery of atrial defibrillation therapy more hazardous or requires lengthening of the shockable R-R interval. In the latter case, however, the ventricular rhythm must decelerate to an even slower rate before a shock can be delivered. If the ventricular rhythm does not slow to the safe rate in a short time, the delay in delivering atrial defibrillation therapy may be deleterious to the patient. Overcoming these problems is an objective of the present invention.

SUMMARY

The present invention relates to a device and method for delivering defibrillation shock therapy in order to treat atrial and/or ventricular tachyarrhythmias in which biventricular pacing is employed to reduce the electrical dispersion brought about by ventricular conduction disorders. Such reduction facilitates the safe delivery of defibrillation shocks synchronously with sensed R waves at a defined shockable R-R interval.

DETAILED DESCRIPTION

The present invention relates to a method and device for delivering defibrillation shock therapy. As used herein, defibrillation shock therapy should be taken to mean shock therapy for treating any tachyarrhythmia, such as atrial flutter, atrial fibrillation, or ventricular tachycardia. As the terms are usually used, a defibrillation shock is a shock delivered without regard to intrinsic cardiac activity, while a shock delivered synchronously with intrinsic activity is referred to as a conversion shock. As used herein, however, a defibrillation shock should be taken to mean either type of shock.

Figure 1:
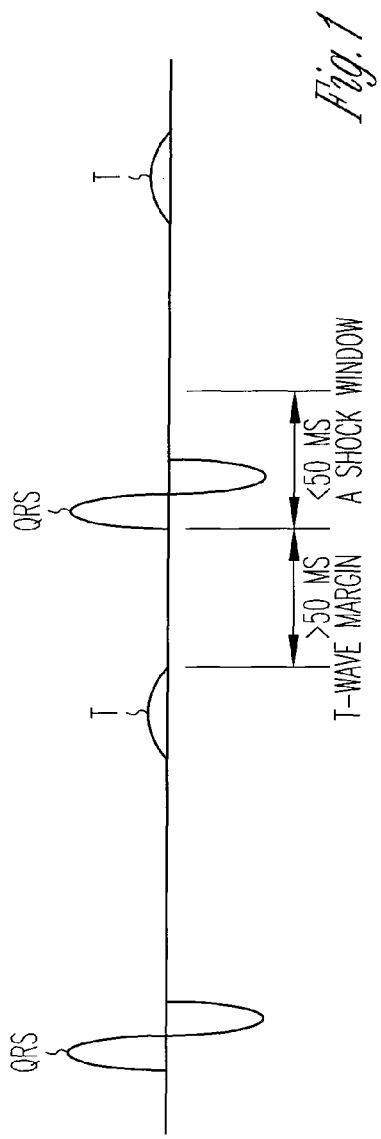
FIG. 1 is a diagram of an ECG illustrating the T wave margin.

In order to avoid the possible induction of ventricular fibrillation, defibrillation shocks used to treat atrial tachyarrhythmias are usually delivered synchronously with a sensed R wave and after a minimum pre-shock R-R interval, where the R-R interval is the time between the immediately preceding R wave and the presently sensed R wave, and where an R wave may be regarded as either a spontaneously occurring depolarization or a ventricular pace. Certain ventricular tachycardias may also be treated with similarly delivered synchronous defibrillation shocks. Although an R wave usually refers to a specific morphological feature of a surface ECG, as used herein, the term R wave should be taken to mean any part of an electrogram or ECG signal which is interpreted as ventricular depolarization. Synchronous shocking with a minimum R-R interval is done because the ventricle is especially vulnerable to induction of fibrillation by a depolarizing shock delivered at a time too near the end of the preceding ventricular contraction (i.e., close to the T wave on an ECG). FIG. 1 illustrates the situation in an example surface ECG where two QRS complexes (i.e., a combination of Q, R, and S waves) representing ventricular depolarization are each followed by a T wave representing ventricular repolarization. As long as a QRS complex occurs after the end of the preceding T wave, it is theoretically safe to shock during a shock window following the QRS complex (shown in the figure as 50 ms) during which time the ventricles are refractory and at the end of which the so-called vulnerable period begins. As shown in FIG. 1, shocking synchronously with the R wave following the first T wave thus provides a safety margin for the shock equal to the interval between the T wave and the start of the next depolarization, referred to as the T wave margin or TQ interval. As the ventricular rate increases, however, the T wave margin decreases. In order to maintain an adequate T wave margin (e.g., 50 ms as shown in the figure), synchronous shocks should only be delivered if the R-R interval is above a specified limit value. Shocking is therefore delayed after detection of an atrial tachyarrhythmia until the ventricular rhythm is slow enough to safely deliver the defibrillation pulse as determined by measuring the R-R interval.

Figure 2:
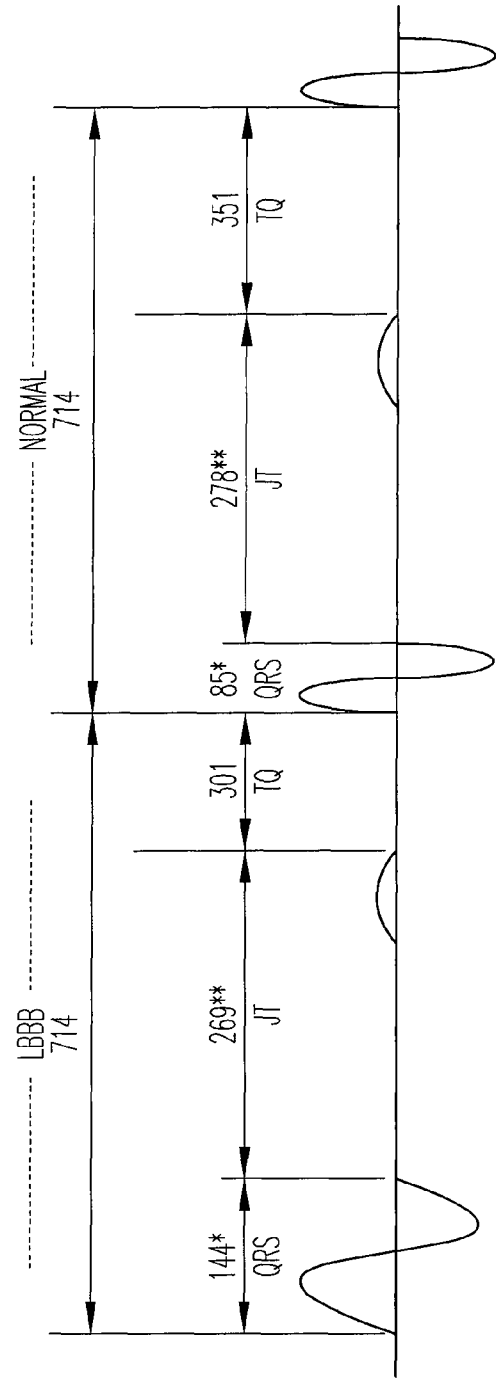
FIG. 2 is a diagram of an ECG showing cardiac cycles with normal and abnormal ventricular conduction.

Ventricular rate, however, is not the only thing which may affect the T wave margin. Certain people, especially heart failure patients, suffer from inter-ventricular conduction disorders (e.g., left bundle branch block or LBBB) which cause dispersion of ventricular depolarization during a ventricular beat as manifested by prolongation of the QRS complex on an ECG. It has been experimentally shown that such conduction disorders result in a shortening of the T wave margin for shocks delivered synchronously with R waves. FIG. 2 illustrates this phenomenon by showing an ECG waveform in which abnormal ventricular conduction due to LBBB occurs in the first cardiac cycle and normal ventricular conduction occurs in the second cycle. Each cardiac cycle is made up of a QRS interval representing the width of the QRS complex, a JT interval from the end of the QRS complex to the end of the subsequent T wave, and the TQ interval from the end of the T wave to the start of the next QRS complex. As shown in the figure, the QRS interval of the LBBB cardiac cycle is longer than the QRS interval of the normal cycle. The JT interval is not affected, however, and the TQ interval (i.e., the T wave margin) is shortened in the LBBB cycle as compared with the normal cycle. This means that the safety margin for delivering a defibrillation shock synchronously with an R wave is decreased in patients who exhibit an inter-ventricular conduction delay. As noted above, this condition is especially prevalent in heart failure patients, and atrial fibrillation is present in 30-40% of heart failure patients which complicates the treatment of atrial tachyarrhythmias in those patients by defibrillation therapy. The present invention deals with this problem by employing ventricular resynchronization pacing to reduce the dispersion of the QRS complex during an atrial tachyarrhythmia. Such ventricular resynchronization pacing allows defibrillation therapy to be delivered more quickly after detection of a tachyarrhythmia and during more types of ventricular rhythms. A detailed description of the invention is set forth below after a description of an exemplary hardware platform and cardiac resynchronization pacing.

1. Exemplary Device Description

Figure 3:
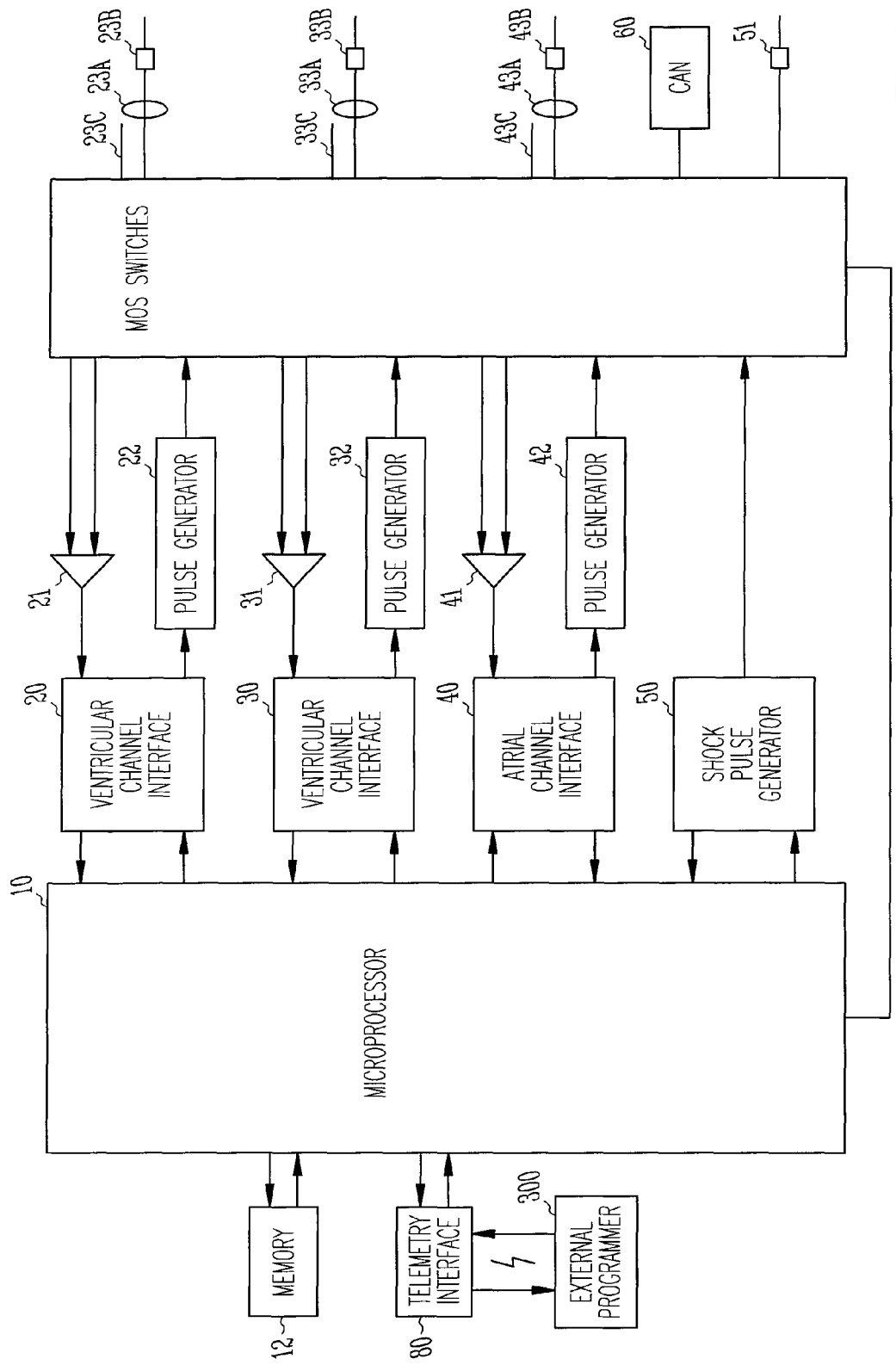
FIG. 3 is a system diagram of exemplary hardware components for delivering cardiac resynchronization therapy and atrial cardioversion therapy.

FIG. 3 is a system diagram of a microprocessor-based implantable cardioverter/defibrillator device for treating atrial tachyarrhythmias that also incorporates a pacing functionality. Such a device is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site. The controller of the device is made up of a microprocessor 10 communicating with a memory 12 via a bidirectional data bus, where the memory 12 typically comprises a ROM (read-only memory) and/or a RAM (random-access memory). The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller interprets electrogram signals from the sensing channels and controls the delivery of pacing and shock pulses. A telemetry interface 80 is provided for communicating with an external programmer 300.

The embodiment shown in FIG. 3 has three sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing with or without atrial tracking, biventricular pacing, or multi-site pacing of a single chamber. In an example configuration, a right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20, and a left ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60. A shock pulse generator 50 is provided for delivering a defibrillation shock pulse to the heart via a shock electrode 51 (referenced to the can or another electrode).

The sensing circuitry of the device generates atrial and ventricular electrogram signals from the voltages sensed by the electrodes of a particular channel. When an electrogram signal in an atrial or ventricular sensing channel exceeds a specified threshold, the controller detects an atrial or ventricular sense, respectively, which pacing algorithms may employ to trigger or inhibit pacing. By measuring the interval between senses in a sensing channel, atrial and/or ventricular tachyarrhythmias can be detected using a rate criterion. The device can be configured to deliver defibrillation shock therapy for treating atrial and/or ventricular tachyarrhythmias by appropriate programming of the microprocessor. For example, if atrial fibrillation is detected with the atrial sensing channel, the device may be programmed to prepare to deliver an atrial defibrillation shock by monitoring the ventricular rhythm so that an atrial defibrillation shock pulse can be delivered synchronously with a sensed R wave if a shockable R-R interval is measured. As described below, the device may also be programmed to initiate biventricular pacing therapy.

2. Cardiac Resynchronization Pacing Therapy

Some heart failure patients suffer from intraventricular and/or inter-ventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Cardiac resynchronization therapy is pacing stimulation applied to one or more heart chambers in a manner that compensates for conduction delays. Ventricular resynchronization pacing is useful in treating heart failure in patients with inter-ventricular or intra-ventricular conduction defects because, although not directly inotropic, resynchronization results in a more coordinated contraction of the ventricles with improved pumping efficiency and increased cardiac output. Resynchronization pacing may involve biventricular pacing with the paces to right and left ventricles delivered either simultaneously or sequentially (where the interval between the paces is defined by a negative, positive, or zero biventricular offset interval), termed biventricular offset pacing. Biventricular pacing can also be delivered with a pace to one ventricle triggered by a sense in the contralateral ventricle, termed herein biventricular pacing even if only one ventricle is used to trigger a pace.

Biventricular offset pacing is most conveniently delivered in conjunction with a bradycardia pacing mode. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the atrio-ventricular pacing delay interval or AVD, where a ventricular pacing pulse is delivered upon expiration of the atrio-ventricular pacing delay interval if no ventricular sense occurs before. In an atrial tracking mode, the atrio-ventricular pacing delay interval is triggered by an atrial sense and stopped by a ventricular sense or pace.

3. Delivery of Ventricular Resynchronization Therapy in Conjunction with Defibrillation Therapy Besides providing a more coordinated mechanical contraction as described above, ventricular resynchronization therapy, by pre-exciting regions of the ventricles which would otherwise depolarize later due to the inter-ventricular or intra-ventricular conduction deficit, also has the salutary effect of reducing the electrical dispersion during ventricular systole which would otherwise occur. This results in an increase in the TQ interval which represents the shockable safety margin of a defibrillation shock delivered synchronously with an R wave and relaxes the rhythm constraints which should otherwise be applied before atrial defibrillation therapy is delivered. In accordance with the present invention, biventricular pacing therapy is used to reduce the electrical dispersion brought about by a ventricular conduction disorder (also referred to as QRS dispersion) and facilitate the safe delivery of a defibrillation shock synchronously with an R wave. The invention may be employed in conjunction with atrial defibrillation shock therapy and may also be employed in conjunction with the delivery of synchronous defibrillation shocks for treating ventricular tachyarrhythmias such as ventricular tachycardia.

In an example embodiment, the invention is incorporated into an ICD with the capability of delivering ventricular resynchronization therapy such as illustrated in FIG. 3 by appropriate programming of the controller. After detecting the presence of an atrial tachyarrhythmia via an atrial sensing channel (or the presence of a ventricular tachyarrhythmia via a ventricular sensing channel for which conversion shock therapy is to be applied), ventricular pacing which reduces QRS dispersion is delivered. A defibrillation shock pulse is then delivered after a predetermined time following the ventricular pacing, where the predetermined time is selected in order to provide an adequate safety margin. The defibrillation shock may be delivered in synchrony with a subsequent intrinsic ventricular beat or in synchrony with a ventricular pace, in which case the predetermined time may be referred to as a shockable RR interval. Alternatively, the defibrillation shock may be delivered at a predetermined instant after the ventricular pacing to reduce QRS dispersion has ended if no intervening intrinsic ventricular beat occurs. Pacing therapy which reduces QRS dispersion is pacing therapy which reduces the QRS dispersion exhibited by intrinsic beats or a previous mode of pacing therapy. The kind of pacing therapy which reduces QRS dispersion depends upon the conduction system of the individual patient and may be, for example, single-site ventricular pacing delivered to the right or left ventricle, ventricular septum pacing, multi-site pacing delivered to one ventricle, or pacing delivered to each ventricle (i.e., biventricular pacing with a specified biventricular offset interval) where the pacing to each ventricle may be multi-site or single-site. The selection of a pacing mode for reducing QRS dispersion may be informed by a measurement of a patient's interventricular and/or intraventricular conduction delay to determine which ventricle or ventricular site should be pre-excited by ventricular pacing in order to reduce QRS dispersion. Measurement of the ventricular delay, in the context of this document, should be taken to mean an estimate of the magnitude and character (e.g., which ventricle is delayed) of the conduction delay with sufficient precision to make an informed decision as to therapy. A clinician may measure the ventricular conduction delay and then program the implantable device appropriately, or the implantable device may be programmed to measure the ventricular conduction delay and automatically configure itself to deliver the appropriate ventricular pacing for reducing QRS dispersion. The ventricular pacing may be delivered for one cardiac cycle or a specified number of cardiac cycles before delivery of the shock pulse. In another variation, a specified number of R waves are required to be sensed without detecting an R-R interval longer than a specified minimum limit value before the ventricular pacing is initiated, where a synchronous defibrillation shock may be delivered upon detection of an R-R interval longer than the specified limit value (i.e., a shockable R-R interval). The ventricular pacing may delivered in an inhibited demand mode with a ventricular escape interval selected to be shorter than the intrinsic R-R interval or in a triggered mode where a sense at a first ventricular site triggers a pace to a second ventricular site or sites.

In one specific embodiment, device delivers biventricular pacing therapy during one or more cardiac cycles after detecting an atrial tachyarrhythmia. The device then senses a ventricular depolarization (R wave) after a biventricular pace and measures the R-R interval. If the R-R interval is longer than a specified minimum limit value and hence shockable, the device delivers a defibrillation shock pulse synchronously with the sensed R wave. In one variation, the device attempts to deliver a defibrillation shock synchronously with a sensed R wave at a shockable R-R interval before initiating biventricular pacing and is programmed to sense a predetermined number of R waves without a shockable R-R interval being detected before initiating biventricular pacing. In another embodiment, the device is programmed to deliver biventricular pacing therapy during one or more cardiac cycles after detecting the presence of a tachyarrhythmia, and then to deliver a defibrillation shock pulse synchronously with a subsequent biventricular pace delivered at a shockable R-R interval. The biventricular pacing may be delivered either as triggered biventricular pacing where a sense in one ventricle triggers a pace to the contralateral ventricle or as biventricular offset pacing. In the latter case the biventricular pacing is delivered in an inhibited demand mode after expiration of a ventricular escape interval since atrial triggered modes cannot be used during an atrial tachyarrhythmia. Since the ventricular rate is usually very fast during an atrial tachyarrhythmia, the ventricular escape interval can either selected to be shorter than a measured R-R interval, or an overdrive pacing or ventricular rate regularization algorithm can be employed to deliver the biventricular pacing.

In another embodiment, the device is programmed to switch from a first type of ventricular pacing to a second type of ventricular pacing after detecting the presence of an atrial tachyarrhythmia, where the QRS dispersion resulting from the first type of ventricular pacing is greater than the QRS dispersion resulting from the second type of ventricular pacing. A defibrillation shock pulse may then be delivered after a predetermined time following a pacing pulse of the second type of ventricular pacing. For example, the first type of ventricular pacing may be right ventricular pacing, and the second type of ventricular pacing may be left ventricular pacing, biventricular pacing, ventricular septum pacing, or ventricular pacing delivered in a triggered mode such that a sense at a first ventricular site triggers a pace to a second ventricular site. Also, since the second type of ventricular pacing reduces QRS dispersion relative to the first type of ventricular pacing only during paced cycles, the second type of pacing may also include an increase in the frequency of pacing by, for example, using a shortened ventricular escape interval in an inhibited demand pacing mode and/or a triggered pacing mode. In a person with normal ventricular conduction, intrinsic beats exhibit less QRS dispersion than paced ones. Therefore, in another embodiment, the second type of ventricular pacing may be QRS dispersion reducing as compared with the first type because the second type of ventricular pacing allows more intrinsic beats to occur. The second type of ventricular pacing may thus include a reduced pacing frequency implemented by, for example, a lengthened ventricular escape interval.

In another embodiment, an apparatus or system is programmed to measure an inter-ventricular or intra-ventricular conduction delay in a patient by sensing at a first and a second ventricular site and measuring a ventricular conduction delay as the time difference between a sense at the first ventricular site and a sense at a second ventricular site. For example, an inter-ventricular conduction delay may be measured as the time difference between right and left ventricular senses detected in its sensing channels during a ventricular beat. QRS dispersion reducing pacing such as biventricular pacing may then be employed during an arrhythmia only if the measured ventricular conduction delay exceeds a specified threshold value. As noted above, the ventricular conduction delay measurement may also be used to select the appropriate pacing mode for QRS dispersion reduction. The specified minimum limit value which defines a shockable R-R interval can also be adjusted in accordance with the measured ventricular conduction delay by, for example, multiplying a programmed nominal value of the limit by a proportionality factor based upon the measured ventricular conduction delay. The system programmed to measure the ventricular conduction delay and perform the steps enumerated above may be made up of an external programmer in communication with the implantable device or the implantable device alone. In the former case, the implantable device transmits data collected from its sensing channels to the external programmer, and the processing for computing the ventricular conduction delay, deciding whether to employ QRS dispersion reducing pacing during an arrhythmia, selecting the appropriate pacing mode for reducing QRS dispersion, and/or adjusting the value of the specified minimum limit may be shared in any desired proportions between the implantable device and the external programmer (or a clinician operating the external programmer). Also, in an alternative embodiment, the patient's ventricular conduction delay may be identified and measured by means other than the implantable device's sensing channels, such as by examining a surface ECG. Such examination of a surface ECG may be done by a clinician or automatically by the external programmer, with the implantable device then programmed appropriately as described above.

Figure 4:
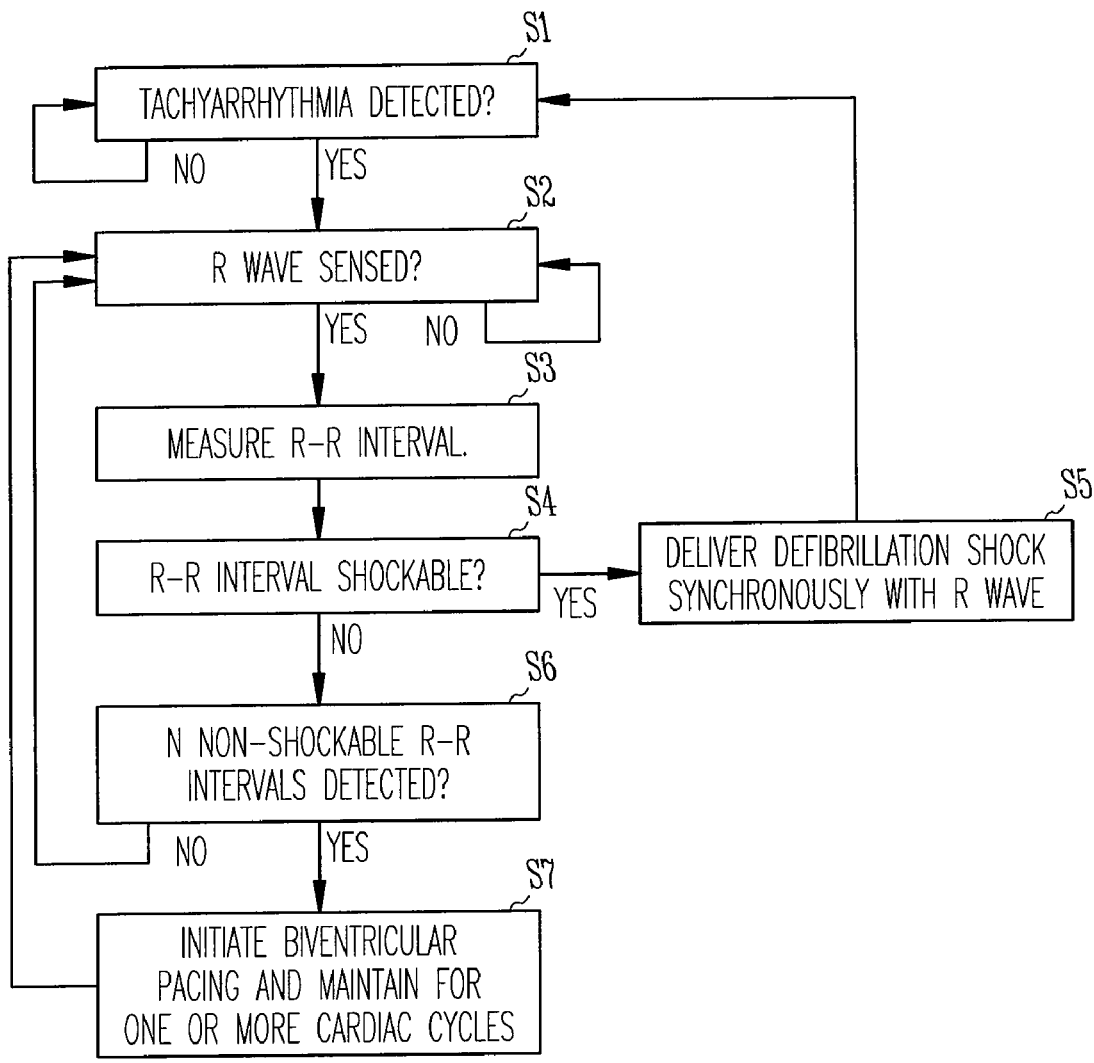
FIG. 4 illustrates an exemplary algorithm for delivering atrial defibrillation therapy.

FIG. 4 illustrates an exemplary algorithm which could be implemented in the ICD of FIG. 3. At step S1, the device monitors a sensing channel (either an atrial or ventricular channel) for the presence of a tachyarrhythmia. Upon detection of a tachyarrhythmia, the device monitors a ventricular sensing channel for sensed R waves at step S2, and measures an R-R interval for a sensed R wave at step S3. If the R-R interval is shockable as determined at step S4, the device delivers a defibrillation shock synchronously with the sensed R wave at step S5 and returns to step S1. If the R-R interval is not shockable, step S6 determines if N non-shockable R-R intervals have been detected. If not, the device returns to step S2 to wait for another R wave. If N non-shockable R-R intervals have been detected, the device initiates biventricular pacing at step S7, and maintains the biventricular pacing for one or more cardiac cycles. The device then returns to step S2 to wait for an R wave and deliver a defibrillation shock if a shockable R-R interval is detected.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for delivering ventricular cardioversion therapy to a patient, comprising:
    identifying the patient as having a ventricular conduction deficit by measuring the patient's ventricular conduction delay; and,
    configuring an implantable cardiac rhythm management device implanted in the patient to detect the presence of a ventricular tachyarrhythmia and, in response thereto, to:
    initiate delivery of ventricular pacing in a selected pacing mode which reduces QRS dispersion from that exhibited by an intrinsic beat in the patient; and,
    deliver a cardioversion shock after a predetermined time interval following a ventricular pace.

2. The method of claim 1 wherein the ventricular pacing is a multi-site pacing mode.

3. The method of claim 2 wherein the multi-site pacing mode includes pacing at least one right ventricular site and at least one left ventricular site.

4. The method of claim 1 wherein the cardioversion shock is delivered synchronously with a sensed R wave if an R-R interval is longer than a specified minimum limit value.

5. The method of claim 1 further comprising delivering a ventricular pacing pulse synchronously with the cardioversion shock.

6. The method of claim 1 further comprising delivering a sequence of multiple ventricular paces before delivering a shock pulse.

7. The method of claim 1 wherein the ventricular pacing is delivered in a left ventricle-only or biventricular pacing mode.

8. A method for delivering ventricular cardioversion therapy, comprising:
    detecting the presence of a ventricular tachyarrhythmia;
    delivering a first type of ventricular pacing while no ventricular tachyarrhythmia is detected;
    delivering a second type of ventricular pacing while a ventricular tachyarrhythmia is detected;
    wherein the QRS dispersion resulting from the first type of ventricular pacing is greater than the QRS dispersion resulting from the second type of ventricular pacing; and,
    delivering a cardioversion shock pulse within a predetermined time after a pacing pulse of the second type of ventricular pacing.

9. The method of claim 8 wherein the first type of ventricular pacing is right ventricular pacing.

10. The method of claim 8 wherein the second type of ventricular pacing is left ventricular pacing.

11. The method of claim 8 wherein the second type of ventricular pacing is biventricular pacing.

12. A device for delivering ventricular cardioversion therapy, comprising:
    sensing circuitry for sensing cardiac electrical activity;
    pulse generation circuitry for generating pacing pulses and shock pulses;
    a controller for controlling the operation of the device;
    a switching network operable by the controller for connecting the pulse generation circuitry and sensing circuitry to selected electrodes in order to configure selected sensing and pacing channels
    wherein the controller is programmed to:
    configure a sensing channel for detecting the presence of a ventricular tachyarrhythmia and configure sensing/pacing channels for delivering biventricular pacing therapy and sensing ventricular depolarizations (R waves);
    initiate ventricular pacing in a mode which includes pacing of the left ventricle after detection of a tachyarrhythmia;
    sense an R wave after a ventricular pace and measure an R-R interval; and,
    deliver a cardioversion shock pulse synchronously with the sensed R wave if the R-R interval is longer than a specified minimum limit value.

13. The device of claim 12 wherein the controller is programmed to deliver ventricular pacing in a multi-site pacing mode.

14. The device of claim 13 wherein the multi-site pacing mode includes pacing at least one right ventricular site and at least one left ventricular site.

15. The device of claim 12 wherein the controller is programmed to deliver a ventricular pacing pulse synchronously with the cardioversion shock.

16. The device of claim 12 wherein controller is programmed to deliver the ventricular pacing in a left ventricle-only or biventricular pacing mode.

17. A device for delivering ventricular cardioversion therapy, comprising:
    sensing circuitry for sensing cardiac electrical activity;
    pulse generation circuitry for generating pacing pulses and shock pulses;
    a controller for controlling the operation of the device;
    a switching network operable by the controller for connecting the pulse generation circuitry and sensing circuitry to selected electrodes in order to configure selected sensing and pacing channels
    wherein the controller is programmed to:
    configure a sensing channel for detecting the presence of a ventricular tachyarrhythmia and configure sensing/pacing channels for delivering a first and a second type of ventricular pacing, wherein QRS dispersion resulting from the first type of ventricular pacing is greater than QRS dispersion resulting from the second type of ventricular pacing;
    deliver a first type of ventricular pacing while no ventricular tachyarrhythmia is detected;
    deliver a second type of ventricular pacing while a ventricular tachyarrhythmia is detected; and,
    deliver a cardioversion shock pulse within a predetermined time after a pacing pulse of the second type of ventricular pacing.

18. The device of claim 17 wherein the first type of ventricular pacing is right ventricular pacing.

19. The device of claim 17 wherein the second type of ventricular pacing is left ventricular pacing.

20. The device of claim 17 wherein the second type of ventricular pacing is biventricular pacing.

* * * * *